United States Patent [19]

Slaikeu et al.

[11] Patent Number: 5,443,907
[45] Date of Patent: Aug. 22, 1995

[54] COATING FOR MEDICAL INSERTION GUIDES

[75] Inventors: Paul Slaikeu, Vadnais Heights; Paul H. Burmeister, White Bear Lake; Richard E. Cappetta, Plymouth; Steven S. Hackett, Minnetonka, all of Minn.

[73] Assignee: Scimed Life Systems, Inc., Maple Grove, Minn.

[21] Appl. No.: 350,714

[22] Filed: Dec. 7, 1994

Related U.S. Application Data

[63] Continuation of Ser. No. 25,720, Mar. 2, 1993, abandoned, which is a continuation of Ser. No. 799,449, Nov. 27, 1991, abandoned, which is a continuation-in-part of Ser. No. 716,678, Jun. 18, 1991, abandoned.

[51] Int. Cl.$^6$ ............................................. D02G 3/00
[52] U.S. Cl. .................................... 428/375; 428/394; 428/395; 604/172; 604/165; 128/657; 128/772
[58] Field of Search ................ 428/375, 394, 395; 604/172, 165; 128/657, 772

[56] References Cited

U.S. PATENT DOCUMENTS

| | | | |
|---|---|---|---|
| 3,216,983 | 11/1965 | Shelanski | 260/88.3 |
| 3,661,634 | 5/1972 | Riley et al. | 117/161 UA |
| 3,695,921 | 10/1972 | Shepherd et al. | 117/72 |
| 3,861,396 | 1/1975 | Vaillancourt et al. | 128/350 R |
| 3,896,753 | 7/1975 | Shepherd et al. | 114/67 R |
| 3,939,049 | 2/1976 | Ratner et al. | 204/159.13 |
| 4,055,682 | 10/1977 | Merrill | 427/2 |
| 4,087,567 | 5/1978 | Sullivan | 427/2 |
| 4,100,309 | 7/1978 | Micklus et al. | 427/2 |
| 4,112,925 | 9/1978 | Sullivan | 128/2 F |
| 4,119,094 | 10/1978 | Micklus et al. | 128/132 R |
| 4,143,423 | 3/1979 | Sternlieb | 2/168 |
| 4,169,163 | 9/1979 | Judd et al. | 426/413 |
| 4,239,664 | 12/1980 | Teng et al. | 260/17.4 R |
| 4,345,602 | 8/1982 | Yoshimura et al. | 128/349 |
| 4,373,009 | 2/1983 | Winn | 428/424.2 |
| 4,381,008 | 4/1983 | Thomas et al. | 604/265 |
| 4,384,954 | 5/1983 | Nakashima et al. | 210/287 |
| 4,456,017 | 6/1984 | Miles | 128/772 |
| 4,459,317 | 7/1984 | Lambert | 427/2 |
| 4,482,577 | 11/1984 | Goldstein et al. | 427/2 |
| 4,487,808 | 12/1984 | Lambert | 428/423.1 |
| 4,534,363 | 8/1985 | Gold | 128/772 |
| 4,557,724 | 12/1985 | Gregonis et al. | 604/49 |
| 4,585,666 | 4/1986 | Lambert | 427/2 |
| 4,589,873 | 5/1986 | Schwartz et al. | 604/265 |
| 4,642,267 | 2/1987 | Creasy et al. | 428/413 |
| 4,666,437 | 5/1987 | Lambert | 523/113 |
| 4,682,607 | 7/1987 | Vaillancourt et al. | 128/772 |
| 4,721,117 | 1/1988 | Mar et al. | 128/772 |

FOREIGN PATENT DOCUMENTS

| | | |
|---|---|---|
| 0340304 | 11/1989 | European Pat. Off. |
| 0380102 | 8/1990 | European Pat. Off. |
| 0405823 | 1/1991 | European Pat. Off. |
| 0407965 | 1/1991 | European Pat. Off. |
| 83118796 | 1/1985 | Japan |
| 88334359 | 7/1990 | Japan |
| 1600963 | 10/1981 | United Kingdom |
| WO85/01444 | 4/1985 | WIPO |
| WO89/09626 | 10/1989 | WIPO |

*Primary Examiner*—N. Edwards
*Attorney, Agent, or Firm*—Vidas, Arrett & Steinkraus

[57] ABSTRACT

An improved guide for a medical insertion device includes a core, a jacket of hydrophobic polymer surrounding the core, and a mixture of hydrophobic and hydrophilic polymer coated onto the jacket. The hydrophobic polymer of the coating is the same as or compatible with the hydrophobic polymer of the jacket, resulting in improved bonding between the jacket and coating. The hydrophilic polymer of the coating provides a slippery surface which facilitates insertion of the device into a vein or other organ. The hydrophilic polymer has reduced tendency to leach or dissolve away, because it is ensnared with the hydrophobic polymer of the coating.

(List continued on next page.)

9 Claims, 1 Drawing Sheet

U.S. PATENT DOCUMENTS

| | | |
|---|---|---|
| 4,729,914 | 3/1988 | Kliment et al. ............... 428/36 |
| 4,739,768 | 4/1988 | Elgelson ....................... 128/655 |
| 4,758,475 | 7/1988 | Eckes et al. ................. 428/423.1 |
| 4,769,013 | 9/1988 | Lorenz et al. ................ 604/265 |
| 4,781,703 | 11/1988 | Walker et al. ................ 604/264 |
| 4,811,743 | 3/1989 | Stevens ........................ 128/772 |
| 4,835,003 | 5/1989 | Becker et al. ................ 427/2 |
| 4,841,976 | 6/1989 | Packard et al. ............... 128/657 |
| 4,867,174 | 9/1989 | Skribiski ...................... 128/772 |
| 4,872,867 | 10/1989 | Joh ................................. 604/269 |
| 4,883,699 | 11/1989 | Aniuk et al. ................. 428/36.9 |
| 4,884,579 | 12/1989 | Engelson ...................... 128/772 |
| 4,899,787 | 2/1990 | Ouchie et al. ................ 138/131 |
| 4,906,237 | 3/1990 | Johansson et al. .......... 604/265 |
| 4,925,445 | 5/1990 | Sakamoto et al. ........... 604/95 |
| 4,950,257 | 8/1990 | Hibb et al. ................... 604/265 |
| 4,955,862 | 9/1990 | Sepetka ........................ 604/164 |
| 4,961,731 | 10/1990 | Bodicky et al. .............. 604/264 |
| 4,977,901 | 12/1990 | Ofstead ........................ 128/772 |
| 4,990,357 | 2/1991 | Karakelle et al. ........... 427/2 |
| 4,991,602 | 2/1991 | Amplatz et al. ............. 128/772 |
| 5,001,009 | 3/1991 | Whitbourne .................. 428/412 |
| 5,041,100 | 8/1991 | Rowland et al. ............. 604/265 |
| 5,047,045 | 9/1991 | Arney et al. ................. 606/144 |
| 5,061,254 | 10/1991 | Karakelle et al. ........... 604/265 |
| 5,069,226 | 12/1991 | Yamauchi et al. ........... 128/772 |
| 5,084,315 | 1/1992 | Karimi et al. ................ 428/36.6 |

OTHER PUBLICATIONS

Klempner, "Interprenetrating Polymer Networks", Angew. Chem. Int. Ed. Engl. 17, 97–106 (1978).

Hunter et al., "Surface Modification Of Polyurethane To Promote Long-Term Potency Of Peritonecal Access Devices", Trans. Am. Soff. Intern. Organs, vol. XXIX, 250–254 (1983).

Moore, et al.—"Endovascular Surgery", W. B. Saunders Co. (1989), pp. 157–159.

"Cordis Ducor And The Angiographic System", Cordis Corp. (1973).

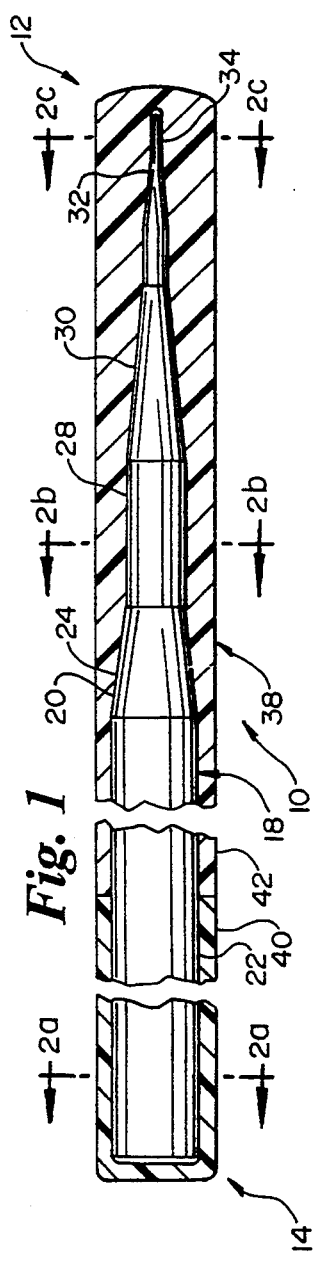
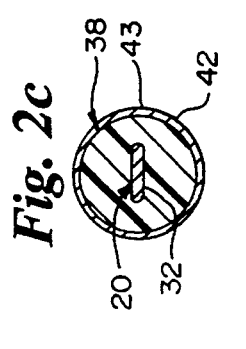
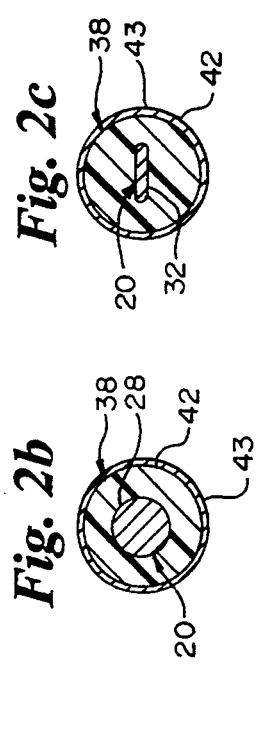
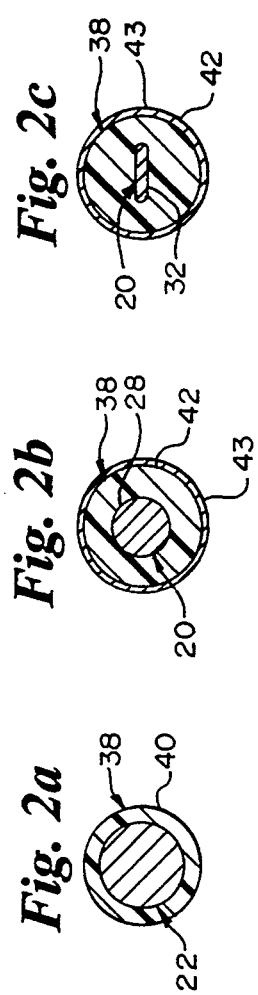
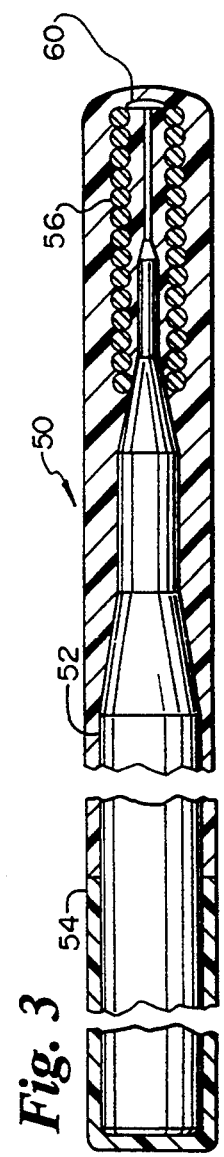
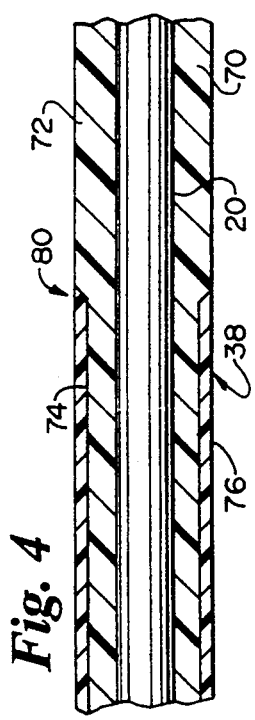

COATING FOR MEDICAL INSERTION GUIDES

RELATED APPLICATIONS

This is a continuation of application Ser. No. 08/025,720, filed on Mar. 2, 1993, now abandoned, which is a continuation of application Ser. No. 07/799,449, filed Nov. 27, 1992, now abandoned, which is a continuation-in-part of U.S. application Ser. No. 07/716,678, filed on Jun. 18, 1991, is now abandoned, the entire disclosure of which is incorporated herein by reference.

FIELD OF THE INVENTION

This invention relates to an improved jacket and coating combination for the guide portions of medical insertion devices such as catheters, probes, guide wires, pacemakers and other devices, which are inserted into the human body for various medical purposes.

BACKGROUND OF THE INVENTION

There is a need in the field of medical insertion devices to provide a slippery yet medically safe surface so that the device can easily be inserted into the human body without causing injury, infection, or excessive discomfort. Usually, the medical insertion device has a guide portion which is inserted into the body first, and whose surface should be exceptionally slippery when wet. The guide portion surface must minimize friction between the guide portion and the inside of the vein or organ, and must also be non-toxic and otherwise chemically inert when exposed to bodily fluids.

Various means for minimizing the surface friction of the guide portions of medical devices are known. U.S. Pat. No. 5,835,003 issued to Becker et al., discloses a medical tubing whose exterior is at least partially covered with a water-activated lubricating coating of a hydrophilic (i.e. water absorbing) thermoplastic resin which is adhesively compatible with the material of the medical tubing. The reference specifically discloses the use of a thermoplastic hydrophilic polyurethane resin. A quantity of polyvinyl pyrrolidone having a molecular weight of at least 200,000 is intimately dispersed and forms a separate phase in the hydrophilic polyurethane. When the coating becomes wet, the hydrophilic polyurethane swells and the polyvinyl pyrrolidone bleeds to the surface to form a lubricating film on the guide portion of the medical device.

U.S. Pat. No. 4,997,901, issued to Ofstead, also discloses medical devices coated with a hydrophilic polymer and lists polyvinyl alcohol which is more than about 88% hydrolyzed, as the preferred hydrophilic polymer.

U.S. Pat. No. 4,884,579, issue to Engelson, discloses a catheter guide wire and lists several polymers that can be used as cover materials to provide a low friction surface. Two of the cover materials listed are polyurethane and polyvinyl pyrrolidone.

U.S. Pat. No. 4,729,914, issued to Kliment et al., discloses the application of N-vinyl pyrrolidone copolymers to a substrate having free isocyanate groups. A chemical reaction then occurs between the N-vinyl pyrrolidone and the isocyanate groups of the substrate, causing the formation of a chemically linked polyvinyl pyrrolidone which has less tendency to leach.

U.S. Pat. No. 4,682,607, issued to Vaillancourt et al., discloses a wire guide provided with a polymer coating which can be a hydrophilic material such as polyvinyl pyrrolidone, polyurethane or hydroxyethyl methacrylate.

European Patent Application 0 405 823A2 discloses generally the use of a hydrophilic coating on the outside surface of a guide wire, to reduce friction.

One of the disadvantages of hydrophilic coatings known in the art is that they tend to leach and can become easily separated from the substrate. Separation can be prevented to some extent by providing for a chemical reaction between the coating and substrate to anchor the hydrophilic coating to the substrate. However, this creates the additional risk that quantities of undesirable, unreacted chemicals will be present in the coating. Thus, there is a need to improve adhesion between hydrophilic coatings and substrates without using a chemical reaction.

SUMMARY OF THE INVENTION

In accordance with the present invention, a medical insertion device is provided which has a distal guide portion that is either composed of or is jacketed with a hydrophobic polymer substrate material. The term "hydrophobic" refers to polymers which lack an affinity for water. Hydrophobic polymers do not dissolve in water when in the thermoplastic state and do not swell or swell only to a limited degree in the presence of water whether in the thermoplastic or crosslinked state. For purposes of the present invention, the term "hydrophobic polymer" includes any polymer which does not dissolve and does not swell more than ten per cent by weight in room temperature water.

The hydrophobic polymer substrate is covered with a hydrophilic coating which is composed of a blend of a hydrophilic polymer and a hydrophobic polymer which is the same as or similar to the substrate. The term "hydrophilic" refers to polymers which have an affinity for water. Hydrophilic polymers tend to dissolve partially or totally in water when in the thermoplastic state, and tend to swell substantially in the presence of water when in the crosslinked state. For purposes of the present invention, the term "hydrophilic polymer" refers to any polymer which is water soluble when not crosslinked, or which is swellable to more than 100% by weight in room temperature water when crosslinked.

By including a hydrophobic polymer in the coating which is the same or similar to the hydrophobic polymer of the substrate, excellent adhesion between the coating and the substrate can be obtained without requiring a chemical reaction to anchor the coating to the substrate. Thus, the risk of having unreacted chemicals present on the surface of the guide portion of the insertion device is overcome. Also, by blending hydrophilic and hydrophobic polymers together, the leaching of the hydrophilic polymer is reduced. The hydrophilic polymer is believed to become ensnared in the hydrophobic medium. Finally, by including a hydrophobic polymer in both the substrate and the coating, the swelling of the guide portion of the medical device inside a vein or organ is reduced.

With the foregoing in mind, it is a feature and advantage of the invention to provide an improved guide portion for a medical insertion device which has a slippery, hydrophilic coating that has excellent adhesion to the guide portion.

It is also a feature and advantage of the invention to provide an improved guide portion for a medical insertion device which does not possess quantities of unreacted chemicals on its outer surface or in the hydrophilic coating thereof.

It is also a feature and advantage of the invention to provide an improved guide portion for a medical insertion device having a slippery, hydrophilic surface which is less prone to leaching and separation of the hydrophilic polymer contained therein.

It is also a feature and advantage of the invention to provide an improved guide portion for a medical insertion device which has a reduced tendency to undergo swelling due to moisture absorption inside a vein or organ.

The foregoing and other features and advantages of the invention will become further apparent from the following detailed description of the presently preferred embodiments, taken in conjunction with the accompanying figures. It is understood that the detailed description and figures are to be construed as illustrative rather than limitative, the scope of the invention being defined by the appended claims and equivalents thereof.

BRIEF DESCRIPTION OF THE FIGURES

FIG. 1 is a sectional view of a first embodiment of the present invention.

FIG. 2a shows a cross section of the embodiment of FIG. 1 along line 2a–2a.

FIG. 2b shows a cross section of the embodiment of FIG. 1 along line 2b–2b.

FIG. 2c shows a cross section of the embodiment of FIG. 1 along line 2c–2c.

FIG. 3 is a sectional view of a second embodiment of the invention.

FIG. 4 is a sectional view of a third embodiment of the invention.

BRIEF DESCRIPTION OF THE PRESENTLY PREFERRED EMBODIMENTS

The present invention is directed toward an improved substrate and coating combination for the distal (i.e. leading) guide portion of any medical insertion device such as catheters, probes, guide wires, pacemakers and other devices, which are inserted for medical purposes into the human body. For purposes of exemplification only, the following detailed description is made with reference to the improved guide wire which is described in the parent U.S. application Ser. No. 07/716,678, filed on Jun. 18, 1991, the entire disclosure of which is incorporated by reference.

Referring to FIG. 1 there is depicted a first preferred embodiment of the present invention. This embodiment is an intravascular guide wire 10. This guide wire 10 has a distal end 12 and a proximal end 14. The guide wire 10 may be approximately 180 centimeters in length and have an outside diameter of approximately 0.035 inches. Other lengths and diameters may be provided so that a range of sizes of guide wires may be available for the different needs of various individual patients and the preferences of physicians. Such other sizes are contemplated within the scope of the present invention and of this embodiment in particular.

The guide wire 10 includes a core 18. The core may be made of a strong, yet flexible material, such as a metal, like stainless steel or nitinol, or other materials, or combinations thereof. In a preferred embodiment, the core 18 is made at least in part of a selectively formable metallic material, as explained in more detail below.

The core 18 extends from the distal end 12 to the proximal end 14 of the guide wire 10.

In a preferred embodiment, the core 18 includes a distal portion 20 and a proximal portion 22. The proximal and distal portions are preferably formed of a single metallic wire. The distal portion 20 has a smaller cross section than the proximal portion 22 to impart greater flexibility to the distal end of the guide wire. In a preferred embodiment, the distal portion 20 of the guide wire comprises a series of stages or regions of tapered portions and portions of uniform cross section, as explained in more detail below. The series of stages of tapered portions and portions of uniform cross section are intended to impart increasing levels of flexibility to the guide wire toward the distal end.

In this embodiment, the proximal portion 22 of the core 18 has a diameter of approximately 0.018 inches. FIG. 2a shows a cross section of the guide wire in the proximal portion 22. The proximal portion 22 of the core 18 extends from a proximal end of the guide wire 10 to a proximal end of the distal portion 20 of the core 18. In this embodiment, the distal portion 20 of the core 18 is approximately 6.75 inches in length.

The distal portion 20 of the core includes a first region 24 immediately adjacent to and distal of the proximal portion 22. The first region 24 of the distal portion 20 of the core is approximately 2.0 inches in length. In the first region 24, the core 18 tapers from the diameter of the proximal portion 20 (e.g. 0.018 inches) to a diameter of approximately 0.0105 inches. In this first region 24, the core has a circular cross section.

The distal portion 20 of the core next includes a second region 28 immediately adjacent to and distal of the first region 24. This second region 28 of the distal portion 20 of the core is approximately 1.0 inches in length. FIG. 2b shows a cross section of the guide wire in this region. The second region 28 is a region of approximately uniform cross section. In this second region 28, the core also preferably has a circular cross section.

The distal portion 20 of the core next includes a third region 30 immediately adjacent to and distal of the second region 28. This third region 30 of the distal portion 20 of the core is approximately 2.0 inches in length. In the third region 30, the core 18 tapers from the diameter of the second region 28 (e.g. 0.0105 inches) to a diameter of approximately 0.00525 inches. In this third region 30, the core also has a circular cross section.

The distal portion 20 of the core next includes a fourth region 32 immediately adjacent to and distal of the third region 30. This fourth region 32 of the distal portion 20 of the core is approximately 1.75 inches in length. In the fourth region 32, the core 18 is flattened toward a distal end 34 thereof to form a ribbon shape having dimensions of approximately 0.010 by 0.00225 inches. FIG. 2c shows a cross section of the guide wire in this region. The ribbon shape of this region causes the guide wire to tend to flex in one plane thereby facilitating the use thereof. In the fourth region 32, the length of the distal flattened portion is approximately 0.5 inches, the length of the portion of circular cross section is approximately 0.7 inches, and a transition zone between these portions has a length of approximately 0.7 inches.

The distal portion 20 of the core wire, including the various regions of tapered and uniform cross section, may be formed by methods known in the art, such as chemical washes, polished, grinding or compressing.

The guide wire 10 also includes a plastic jacket 38 extending from the proximal end 14 to the distal end 12. In a first preferred embodiment, the plastic jacket 38 is formed of a proximal jacket portion 40 and a distal jacket portion 42. The outside diameter of the plastic jacket 38 in this embodiment is approximately 0.035 inches although other diameters may be provided for guide wires of other dimensions.

The distal jacket portion 42 is approximately 20 inches in length and extends proximally from the distal end of the guide wire 10. The distal end of the distal jacket portion 42 extends over and covers the distal end of the core wire 18. The proximal jacket portion 40 extends from the proximal end of the guide wire 10 distally. In this embodiment, the proximal end of the distal jacket portion 42 substantially abuts the distal end of the proximal jacket portion 40. At the location at which the proximal and distal jacket portions abut, the outside diameters of the jacket portions are substantially the same and form a smooth transition at that location so that the guide wire can be readily inserted into and moved within a catheter or vessel or that a catheter or other device can be readily advanced over the guide wire.

These two jacket portions are provided to yield features related to functions specifically associated with their respective locations. In this embodiment, the proximal jacket portion 40 is made of a polytetrafluoroethylene (Teflon ®) material and the distal jacket portion 42 is made of a hydrophobic polymer material such as nylon, polyvinyl chloride, silicone, a fluoroelastomer, hydrophobic polyurethane, polyester, acrylic, polycarbonate, polyimides, or combinations thereof. The preferred material for the distal jacket portion 42 is hydrophobic polyurethane. The proximal jacket portion 40 may also be made of another material or combination of materials such as a fluororesin, high density polyethylene, polyacetal, Hytrel, Pebox, Nylon or polypropylene, or any of the hydrophobic materials listed above.

The distal jacket portion may be loaded with a radiopaque material in the range of 40% to 70%. In one preferred embodiment, the distal jacket portion is loaded with a 60% radiopaque material.

In accordance with the invention, the distal jacket portion 42 has a hydrophilic coating 43 applied to it to make its surface highly lubricous when it comes into contact with a fluid such as blood. The hydrophilic coating is believed to improve the biocompatibility of the guide wire 10. This is based in part on observations that hydrophilic surfaces are generally less thrombogenic. The hydrophilic coating provides a slippery yet medically safe surface so that the guide wire can easily be inserted into the human body without causing injury, infection, or excessive discomfort.

The hydrophilic coating 43 includes a blend of about 10–90 weight per cent of a hydrophobic polymer and about 90–10 weight per cent of a hydrophilic polymer. Preferably, the hydrophilic coating 43 contains about 20–70 weight per cent hydrophobic polymer and about 80–30 weight per cent hydrophilic polymer, most preferably about 30–55 weight per cent hydrophobic polymer and about 70–45 weight per cent hydrophilic polymer. The hydrophobic component provides the coating 43 with an affinity to the hydrophobic substrate 42, while the hydrophilic component is a slippery, otherwise water soluble material. The hydrophilic component tends not to dissolve away because it is ensnared with the water insoluble hydrophobic component.

The hydrophobic polymers which are suitable for use in the hydrophilic coating 43 include any of the aforementioned hydrophobic polymers or combinations thereof which can be used to construct the distal jacket portion 42. Preferably, the hydrophobic component of the hydrophilic coating 43 is the same or very similar to the polymer of the distal jacket portion 42, in order to promote excellent adhesion between the hydrophilic coating 43 and the distal jacket portion 42. Most preferably, the hydrophobic component of the coating 43 is hydrophobic polyurethane, and the distal jacket portion 42 is also of hydrophobic polyurethane. Examples of suitable hydrophobic polyurethanes include Dow Pellethane 2363 series or Thermedics Tecophane or Tecoflex series.

The hydrophilic polymers which are suitable for use in the hydrophilic coating 43 include polyvinyl pyrrolidone, poly (ethylene oxide), poly (acrylic acid), poly (methacrylic acid), polyacrylamide, poly (hydroxyethyl acrylate), poly (hydroxyethyl methacrylate), polyvinyl alcohol, poly (sodium styrene sulfonate), poly (2-acrylamido-2-methylpropane sulfonic acid), poly (sodium vinyl sulfonate), poly (vinyl pyridine), proteins, copolymers of the foregoing, or combinations thereof. The preferred hydrophilic polymer is polyvinyl pyrrolidone. Polyvinyl pyrrolidone is used in many medical and drug applications, is well tolerated by the body, and is easily dissolved in solvent.

The coating material for the hydrophilic coating 43 can be prepared by dissolving both the hydrophobic polymer and the hydrophilic polymer, in the desired ratios, in a solvent system. The selection of a suitable solvent system involves consideration at the hydrophobic and hydrophilic polymer components and of the substrate 42 material which is to be coated. The solvent system should be able to swell or dissolve, in part, the substrate, so that the coating 43 can be securely bonded to the substrate 42.

In the preferred embodiment, one approach is to use an organic solvent for the hydrophobic polyurethane and add enough water or alcohol to dissolve the polyvinyl pyrrolidone. Preferred solvent systems are dimethyl acetamide with water, dimethyl formamide with water, and tetrahydrofuran with water. Other solvent systems (which may in fact become preferred if certain hydrophobic and hydrophilic polymers are used) include hydrocarbons, halogenated solvents, ketones, ethers, amides, and water, in any compatible combinations. Typically, the mixture of solvents and hydrophobic and hydrophilic polymers contains about 0.1 to about 25 weight per cent solids, more commonly about 1 to about 15 weight per cent solids and most commonly about 4 to about 10 weight per cent solids.

In order to form the coating 43, the mixture of solvents with hydrophobic and hydrophilic polymers is applied to the distal jacket portion 42 in an amount sufficient to completely coat the distal jacket portion 42. Then, the solvents are allowed to dry. The coating 43 preferably blends with the substrate so that there is no clear boundary between the coating and the substrate.

In a preferred embodiment, the hydrophilic coating is applied only to a distal portion of the guide wire, and in particular, only to the distal jacket portion 42. This is facilitated because the preferred hydrophilic coating is formulated to adhere to the urethane material of the distal jacket portion but not adhere to many different materials including the preferred material of the proximal jacket.

As mentioned above, the proximal jacket portion is made of polytetrafluoroethylene which also provides a low friction surface though not as low friction as that of the distal jacket portion with the hydrophilic coating applied. It is advantageous for the proximal portion of the guide wire to have a low friction surface in order to traverse a catheter lumen or a vessel. However, because the proximal portion of the guide wire will likely be in a portion of the vasculature not as tortuous as the distal portion, it would not require a surface of as high lubricity as the distal portion and therefore polytetrafluoroethylene or any of the other previously mentioned proximal materials with or without a silicone coating, is a good choice of materials.

Moreover, this combination of low friction surfaces has the additional advantage that a very low friction surface, such as one having a hydrophilic coating, is used only on the distal portion of the guide wire. A very low friction surface, such as one having a hydrophilic coating, would be so slippery that it would be difficult for a physician to handle if it were on the proximal end as well. Accordingly, at the proximal end of the guide wire, this embodiment includes a surface that is easy for the physician who would be manipulating the guide wire from the proximal end to handle and yet is of sufficiently low friction so that it can readily traverse portions of the patient's vessels and provide good guide wire movement in a catheter.

It is also preferred that the distal portion of the guide wire be provided with enhanced radiopaque properties. In the preferred embodiment, this is done by loading the material from which the distal jacket 42 is made with radiopaque materials such as barium, bismuth or tungsten. The loading of the distal jacket of polyurethane with a radiopaque material enhances the ability of a physician to observe the position of the distal end of the guide wire in the body of the patient by means of fluoroscopy.

In a preferred embodiment, the proximal jacket portion 40 of polytetrafluoroethylene is heat shrunk onto the core wire. The distal jacket portion 42 is installed over the core wire by heating a sleeve of polyurethane to a temperature until it is reformed around the core wire. The proximal and distal jackets may be finished by a centerless grinding method so that the transition between the jacket portions is smooth.

In a further embodiment, the guide wire has a core that is selectively formable at least in a distal portion thereof. By a selectively formable core, it is meant that the wire from which the core is made may be bent to a particular shape and that the shape will be maintained by the wire. This allows the physician to impart a particular shape to the guide wire, by bending or kinking it for example, to facilitate its placement into a patient's vasculature. To provide this selective formability, in a preferred embodiment, the entire core wire may be made of stainless steel. Other materials may be used to provide this feature. The use of a formable material, such as stainless steel, provides advantages in the guide wire over materials that cannot be formed, such as superelastic materials like nitinol. Superelastic materials, like nitinol are so resilient that they tend to spring back to their original shape even if bent, thus are not formable. Although superelastic material may be provided with a "preformed" memory shape, such a preformed shape is typically determined in the manufacture of the guide wire and cannot readily be altered or modified by the physician by simply bending the guide wire prior to use. Although use of superelastic materials such as nitinol in guide wire applications may provide some advantages in certain uses, a formable core, such as of stainless steel, which can be formed by the physician to a shape suitable for a particular patient or preferred by that physician, provides an advantage that cannot be obtained with a superelastic core guide wire.

In a further preferred embodiment, the guide wire may include a core wire of a material having formable properties at a distal portion thereof and non-formable (e.g. superelastic properties) proximally. Such a construction would provide advantages in certain guide wire usages. A guide wire having these properties could be formed by using a superelastic material such as nitinol for the core wire and reducing its superelasticity in a distal portion thereof. This may be effected by heating the distal end of the superelastic core wire. Another means to reduce the superelastic properties of a distal end of the core wire would be to shape it mechanically, e.g. flattening it. Other methods of reducing the superelastic properties of the core wire may also be used. With a core wire having this dual combination of a formable distal portion and a superelastic proximal portion, desired shapes could be imparted by a physician to the distal end of the guide wire to facilitate making turns, etc., in tortuous vessel passages, while in the same guide wire the more proximal portion would possess superelastic properties to allow it to follow the distal portion through the tortuous passages without permanently deforming. This combination of formable and non-formable properties in the core wire may also be provided by using more than one material for the core wire or more than one wire.

FIG. 3 shows another preferred embodiment of the present invention. This embodiment of the guide wire is similar in some respects to the embodiment of the guide wire, described above. Although this embodiment of the guide wire may be provided in large sizes (e.g. 0.035 inches), this embodiment is especially suitable for a guide wire of a smaller diameter, e.g. having an outer diameter of approximately 0.018 inches. If provided in a guide wire of smaller diameter, the diameter of the core wire and plastic jacket would be correspondingly smaller. Like the embodiment described above, this guide wire includes a core 52 surrounded by a plastic jacket 54. The core 52 is preferably of a selectively formable material, as described above. In addition, in this embodiment, a marker 56 is provided at a distal end 58 of the guide wire 50. This marker 56 is located around the distal portion of the core wire 52 underneath the plastic jacket 54. In this embodiment, the marker 56 is a coil spring. Alternatively, the marker may be a ribbon, another wire, or any other similar component. A tip 60 may be provided at the distal end of the core wire 52 to facilitate placement and connection of the marker 56.

The marker 56 may be made of platinum or stainless steel or other material. The marker 56 may be provided with radiopaque properties by selecting a material such as platinum. This may be in addition or as an alternative to providing radiopaque properties in the jacket portion through the use of loading with radiopaque materials. The use of a radiopaque marker may be preferred in smaller diameter guide wires where the plastic jacket, even if loaded with a radiopaque material, is of such a small size that it could be difficult to discern under fluoroscopy.

FIG. 4 shows another preferred embodiment of the present invention. In the embodiment in FIG. 4, a core wire 20 extends from a distal to a proximal end of the guide wire. As in the embodiment described above, the core wire 20 is surrounded by a core wire jacket 38. In this embodiment, the core wire jacket 38 is comprised of a first jacket 70. The first jacket 70 of this embodiment is comprised of a first portion 72 and a second portion 74. The core wire jacket 38 also includes a second jacket 76. The second jacket 76 covers the first jacket 70 over the second portion 74 thereof. The second jacket 76 may correspond to the proximal jacket of the previous embodiments. The second jacket 76 may be a thin tubing that is heat shrunk onto the first jacket 70 over a proximal portion thereof. Alternatively, the second jacket 76 may be applied by other methods, such as by spraying, dipping, etc.

In a preferred embodiment, the outer diameter of the second jacket 76 when it is in position surrounding the first jacket 70 is approximately the same as the outer diameter of the first jacket 70 in the first portion 72 thereof at least in an area 80 of the guide wire where the second jacket 76 ends so that the overall diameter of the guide wire through this area 80 is substantially uniform. This uniformity may be further enhanced by polishing, grinding, or other means. To further provide for this uniformity in diameter, the second portion 74 of the first jacket 70 may be provided with a diameter that is less than that of the first portion 72 of the first jacket 70. This reduction in diameter may be formed by grinding, stretching, chemical erosion, or other means.

In a preferred embodiment, the second jacket 76 covers the proximal portion of the guide wire and an exposed first portion 72 of the first jacket 70 extends to a distal end of the guide wire. The first jacket 70 and second jacket 76 may be provided with properties specifically directed to their respective functions, as explained above in regard to the embodiment of the guide wire in which the jackets are in an abutting relationship. For example, the first jacket 70 may be made of polyurethane and the second jacket 76 may be made of a Teflon-like material. A hydrophilic coating may be applied to the first jacket 70 in the first portion 72 thereof to enhance lubricity, as explained above. If this embodiment of the guide wire is intended for use in peripheral regions of the body, it may have an outside diameter of approximately 0.035 inches. Other dimensions may be suitable as well for other size guide wires. As in the previously described embodiments, the core 20 may be a material such as stainless steel or nitinol and may have formable properties in at least a portion thereof.

It is intended that the foregoing detailed description be regarded as illustrated rather than limiting and that it is understood that the following claims including all equivalents are intended to define the scope of the invention.

We claim:

1. A guide for medical insertion device comprising:
a core;
a jacket surrounding the core, the jacket being composed of a hydrophobic polymer; and
a hydrophilic coating applied to the jacket, the hydrophilic coating being composed of a blend of about 10 to about 90 weight percent of a hydrophobic polymer and about 90 to about 10 weight percent of a hydrophilic polymer;
the hydrophilic coating being free of unreacted chemicals;
the guide being free of chemical reaction between the hydrophilic coating and the jacket;
the hydrophobic polymer of the jacket and the hydrophobic polymer of the hydrophilic coating comprising the same polymer, said hydrophobic polymer being selected from the group consisting of nylon, polyvinyl chloride, silicone, fluroelastomers, polyester, acrylic, polycarbonate, polyimides, and combinations thereof; and
the hydrophilic polymer of the coating being selected from the group consisting of polyacrylamide, polyvinyl alcohol, poly(sodium styrene sulfonate), poly(2-acrylamido-2-methylpropane sulfonic acid), poly(sodium vinyl sulfonate), poly(vinyl pyridine), proteins, and combinations thereof.

2. The guide of claim 1, wherein the hydrophilic coating comprises about 20 to about 70 weight per cent of the hydrophobic polymer and about 80 to about 30 weight per cent of the hydrophilic polymer.

3. The guide of claim 1, wherein the hydrophilic coating comprises about 30 to about 55 weight per cent hydrophobic polymer and about 70 to about 45 weight per cent hydrophilic polymer.

4. A guide for medical insertion device comprising:
a core;
a jacket surrounding the core, the jacket comprising a hydrophobic polymer selected from the group consisting of nylon, polyvinyl chloride, silicone, fluroelastomers, polyester, acrylic, polycarbonate, polyimides, and combinations thereof; and
a hydrophilic coating applied to the jacket, the hydrophilic coating comprising a blend of said hydrophobic polymer with a hydrophilic polymer selected from the group consisting of polyacrylamide, polyvinyl alcohol, poly(sodium styrene sulfonate), poly(2-acrylamido-2-methylpropane sulfonic acid), poly(sodium vinyl sulfonate), poly(vinyl pyridine), proteins and combinations thereof;
the hydrophilic coating being free of unreacted chemicals; and
the guide being free of chemical reaction between the hydrophilic coating and the jacket.

5. The guide of claim 1, wherein the hydrophilic polymer comprises polyvinyl pyrrolidone.

6. A guide for medical insertion device comprising:
a core;
a jacket surrounding the core, the jacket being composed of a hydrophobic polymer; and
a hydrophilic coating applied to the jacket, the hydrophilic coating being composed of a blend of about 10 to about 90 weight percent of a hydrophobic polymer and about 90 to about 10 weight percent of polyvinyl pyrrolidone;
the hydrophilic coating being free of unreacted chemicals;
the guide being free of chemical reaction between the hydrophilic coating and the jacket; and
the hydrophobic polymer of the jacket and the hydrophobic polymer of the hydrophilic coating comprising the same polymer, said hydrophobic polymer being selected from the group consisting of nylon, silicone, fluroelastomers, polyester, polycarbonate, polyimides, and combinations thereof.

7. The guide of claim 6, wherein the hydrophilic coating comprises about 20 to about 70 weight per cent of the hydrophobic polymer and about 80 to about 30 weight per cent of polyvinyl pyrrolidone.

8. The guide of claim 6, wherein the hydrophilic coating comprises about 30 to about 55 weight per cent hydrophobic polymer and about 70 to about 45 weight per cent of polyvinyl pyrrolidone.

9. A guide for medical insertion device comprising:
a core;
a jacket surrounding the core, the jacket comprising a hydrophobic polymer selected from the group consisting of nylon, silicone, fluroelastomers, polyester, polycarbonate, polyimides, and combinations thereof; and
a hydrophilic coating applied to the jacket, the hydrophilic coating comprising a blend of said hydrophobic polymer with polyvinyl pyrrolidone;
the hydrophilic coating being free of unreacted chemicals; and
the guide being free of chemical reaction between the hydrophilic coating and the jacket.

* * * * *